United States Patent
Schott et al.

(10) Patent No.: US 11,793,743 B2
(45) Date of Patent: *Oct. 24, 2023

(54) COMPOSITIONS COMPRISING ACETONE, A MONOALCOHOL, GLYCERIN, AND CELLULOSE THICKENER

(71) Applicant: L'OREAL, Paris (FR)

(72) Inventors: Andrea E. Schott, New Providence, NJ (US); Aline Guimont, South Orange, NJ (US); Daniella Gonzalez-Toro, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/397,492

(22) Filed: Apr. 29, 2019

(65) Prior Publication Data

US 2020/0337976 A1   Oct. 29, 2020

(51) Int. Cl.
| | | |
|---|---|---|
| *A61Q 3/04* | (2006.01) | |
| *A61K 8/34* | (2006.01) | |
| *A61K 8/73* | (2006.01) | |
| *A61K 8/35* | (2006.01) | |

(52) U.S. Cl.
CPC .............. *A61K 8/731* (2013.01); *A61K 8/34* (2013.01); *A61K 8/345* (2013.01); *A61K 8/35* (2013.01); *A61Q 3/04* (2013.01)

(58) Field of Classification Search
None
See application file for complete search history.

(56) References Cited

U.S. PATENT DOCUMENTS

| | | | |
|---|---|---|---|
| 4,032,464 A | | 6/1977 | Mausner |
| 4,482,538 A | * | 11/1984 | Davies ............ A61Q 3/02 106/169.56 |
| 4,735,798 A | | 4/1988 | Bernstein |
| 5,139,570 A | * | 8/1992 | Castrogiovanni ....... A61K 8/26 106/3 |
| 5,294,435 A | | 3/1994 | Remz et al. |
| 5,342,536 A | * | 8/1994 | Miner ................ A61K 8/65 510/505 |
| 5,866,104 A | * | 2/1999 | Cataneo ................ 424/61 |
| 7,250,174 B2 | * | 7/2007 | Lee ................ A61Q 11/00 424/404 |
| 9,987,212 B2 | | 6/2018 | MacNeill |
| 2017/0007516 A1 | * | 1/2017 | Mercado ........... A61K 8/342 |

FOREIGN PATENT DOCUMENTS

| | | |
|---|---|---|
| CN | 101953769 A | 1/2011 |
| CN | 105078801 A | 11/2015 |
| JP | 2014139142 A2 | 7/2014 |
| TW | 201210624 A | 3/2012 |

OTHER PUBLICATIONS

Gentle Nail Remover, Mintel GNPD, p. 1-2, Published on Aug. 2012.
Tommy Girl Sugar Scrub, Mintel GNPD, p. 1-2, Published on Nov. 2001.
Orange Nail Remover Jelly, Mintel GNPD, p. 1-3, Published on Feb. 2011.
3in1 Remover, Mintel GNPD, p. 1-2, Published on Nov. 2012.
Nail Polish Remover Gel, Mintel GNPD, p. 1-2, Published on Aug. 2007.
Nail Polish Remover Gel, Mintel GNPD, p. 1-3, Published on Jan. 2013.
Nail Polish Remover Gel, Mintel GNPD, p. 1-2, Published on Feb. 2008.
Acetone Solution Nail Polish Remover, Mintel GNPD, p. 1-3, Published on Jun. 2009.
Acetone-Based Nail Polish Remover, Mintel GNPD, p. 1-2, Published on Jul. 2005.
Nail Polish Remover Gel Ultra Strong, Mintel GNPD, p. 1-2, Published on May 2017.
Nail Renew (Treatment Enamel Remover), Mintel GNPD, p. 1-2, Published on Nov. 2003.
Leave No Trace Glitter Nail Polish Remover, Mintel GNPD, p. 1-2, Published on Jul. 2015.

* cited by examiner

*Primary Examiner* — Celeste A Roney
(74) *Attorney, Agent, or Firm* — Womble Bond Dickinson (US) LLP

(57) ABSTRACT

Compositions are provided for removing nail polish that include a co-mixture that consists of C2-C3 monoalcohol, glycerin, and acetone. The glycerin and the C2-C3 monoalcohol are present in a glycerin to C2-C3 monoalcohol weight ratio of less than about 0.6. The composition further includes a cellulose polymer soluble in said C2-C3 monoalcohol. The concentration by weight of water in the composition is less than the concentration by weight of glycerin.

19 Claims, 1 Drawing Sheet

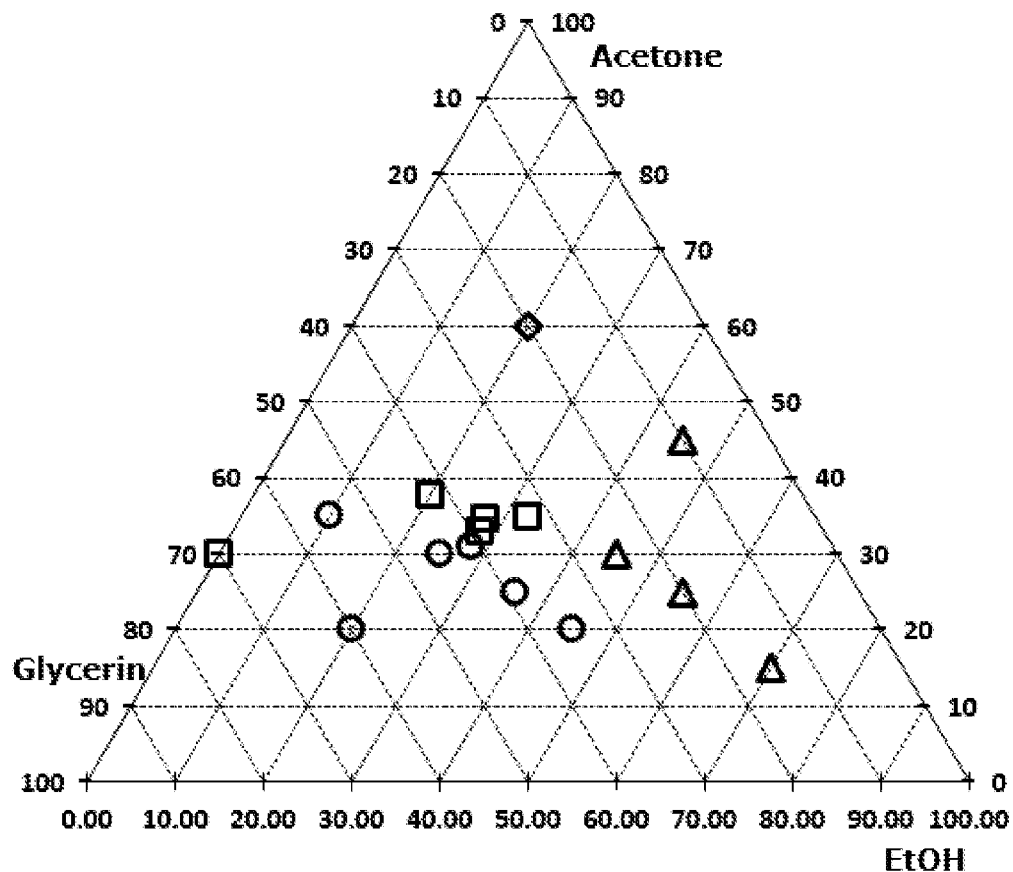

COMPOSITIONS COMPRISING ACETONE, A MONOALCOHOL, GLYCERIN, AND CELLULOSE THICKENER

FIELD OF THE INVENTION

The present invention relates to compositions and methods for removing nail polish.

DISCUSSION OF THE BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails.

In particular, the inventors have recognized the need to provide efficacious nail polish removal using compositions that include highly efficacious solvents such as acetone and alkyl acetates, yet are capable of providing additional benefits such as ease of application, such as ease of application, reduced likelihood of spillage, gentle removal, and improved cosmetic experience.

SUMMARY OF THE INVENTION

The present invention relates to compositions for removing nail polish that include a co-mixture that consists of monoalcohol, glycerin, and acetone. In the co-mixture, the glycerin and the C2-C3 monoalcohol are present in a glycerin to C2-C3 monoalcohol weight ratio of less than about 0.6. The composition further includes a cellulose polymer soluble in said C2-C3 monoalcohol. The concentration by weight of water in the composition is less than the concentration by weight of glycerin.

The present invention also relates to methods for removing nail polish from nails and moisturizing the hands of a subject. The method includes applying a composition to the hands and to nails of a subject onto which the nail polish had been previously applied and removing the nail polish from the nails. The compositions include a co-mixture of monoalcohol, glycerin, and acetone. The composition includes a co-mixture that consists of monoalcohol, glycerin, and acetone. In the co-mixture, the glycerin and the C2-C3 monoalcohol are present in a glycerin to C2-C3 monoalcohol weight ratio of less than about 0.6. The composition further includes a cellulose polymer soluble in said C2-C3 monoalcohol. The concentration by weight of water in the composition is less than the concentration by weight of glycerin.

It is to be understood that both the foregoing general description and the following detailed description are exemplary and explanatory only, and are not restrictive of the invention.

BRIEF DESCRIPTION OF FIGURES

FIG. 1 is a diagram using data developed by the inventors, showing co-mixtures of glycerin, acetone and ethanol, and thickeners used therewith.

DETAILED DESCRIPTION OF THE INVENTION

As used herein, the expression "at least one" means one or more and thus includes individual components as well as mixtures/combinations. All percentages listed are by weight unless otherwise noted.

Furthermore, all concentrations (and concentration ranges) of glycerin, the C2-C3 monoalcohol, and acetone in this specification may apply to just to the co-mixture (described herein) or, in certain embodiments to the entire composition. For example, unless explicitly stated otherwise when the specification states that glycerin may be present in an amount of about 15% to about 60%, not only does this contemplate that range of glycerin concentration in the co-mixture, but it also contemplates that range of concentration of glycerin in the entire composition.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% of the indicated number, such as within 5%, such as within 1% or 2% of the indicated number.

"Essentially free" means that the composition includes less than about 3% of the identified ingredient. "Substantially free" means that the composition contains less than about 2% of the identified ingredient. "Free" means that the composition contains less than 1% of the identified ingredient.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful.

For purposes of the compositions and methods of the present invention where the invention "consists essentially of" the identified ingredients and/or process steps, the two "basic and novel properties" of such compositions and/or methods are "removing nail polish from nails," and "phase stability.

Compositions for Removing Nail Polish

The inventors have found that while glycerin serves as an efficient humectant for moisturizing the skin, glycerin is generally immiscible with acetone and ethyl acetate. However, the inventors have found that certain mixtures of these acetone/alkyl acetate plus C2-C3 monoalcohols and glycerin components along with certain thickeners are indeed capable of being thickened and capable of removing nail polish. The inventors have further surprisingly found that if one desires to thicken such a system, the appropriate choice of thickener depends upon the relative concentrations of glycerin, acetone, and C2-C3 monoalcohol.

Co-Mixture

As described above, compositions of the present invention include a co-mixture that consists of three components: (1) C2-C3 monoalcohol, (2) glycerin, and (3) acetone. While the co-mixture includes no other components than (1), (2), and (3) above, the entire composition may include other components, as described in this specification. Within the composition all C2-C3 monoalcohols, as well as the glycerin and acetone are considered to be part of the co-mixture.

According to certain notable embodiments, the co-mixture exists as a single phase which may or may not include other components.

Glycerin

In accordance with the present invention, compositions for removing nail polish comprising glycerin (a.k.a., glycerol, glycerine, propanetriol, 1,2,3-Trihydroxypropane or 1,2,3-Propanetriol) are provided. By glycerol, it is meant the polyol compound $C_3H_8O_3$, having the general structure below as well as, in certain embodiments, isomers thereof.

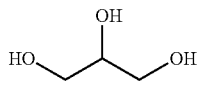

Glycerin may be present in the co-mixtures useful in the present invention in an amount of from about 5%, 10%, 15%, 20%, or 25% by weight to about 25%, 30%, 55%, or 60% by weight. In certain notable embodiments the glycerin is present in a concentration no more than 15%

C2-C3 Monoalcohol

In accordance with the present invention, compositions for removing nail polish comprising a C2-C3 monoalcohol are provided.

"C2-C3 monoalcohol" means an alcohol having 2 or 3 carbon atoms such as ethanol, propanol, and isopropanol. In certain embodiments the C2-C3 monoalcohol is ethanol.

The C2-C3 monoalcohol is present in the co-mixtures useful in the present invention in an amount of from about 5%, 10%, 25% or 30% by weight to about 30%, 40%, 50%, 70% or 90% by weight. In certain notable embodiments, the C2-C3 monoalcohol is present in a concentration of at least about 30%, such as at least about 45%, such as from about 45% to about 70%.

Acetone

In accordance with the present invention, compositions for removing nail polish include acetone as a primary nail polish-removing solvent.

The nail polish-removing solvent may be present in the co-mixtures useful in the present invention in an amount from about 10%, 20%, 25% or 30% to about 40%, 50%, 70% or 85% by weight. In certain embodiments, the concentration of acetone is less than about 55%, such as from about 10% to about 55%, such as from about 15% to about 45% by weight in the co-mixture. In yet other embodiments, in order to provide phase compatibility, the compositions are substantially free of alkylene carbonates such as propylene carbonate.

Glycerin to Acetone Weight Ratio

The inventors have found that co-mixtures useful in the present invention having relatively high concentrations of monoalcohol and/or relatively low concentrations of glycerin can be thickened with cellulose polymers. According to certain embodiments of the invention, the glycerin to acetone weight ratio (i.e., the concentration by weight of glycerin divided by the concentration by weight of acetone) may be less than about 1.2. For sake of clarity, by "glycerin to acetone weight ratio that are less than about 1.2," it is meant that if, for example, the concentration by weight of glycerin is (about) 24% by weight, then the concentration by weight of the acetone is less than (about) 20% by weight.

Glycerin to C2-C3 Monoalcohol Weight Ratio

As discussed, the inventors have further surprisingly identified that sufficiently high levels of glycerin can be beneficially incorporated into thickened compositions including solvents that glycerin is not generally compatible with, like acetone. Accordingly, compositions of the present invention have ratios by weight of glycerin to C2-C4 monoalcohol that is less than about 0.6. For sake of clarity, by "ratios by weight of glycerin to C2-C4 monoalcohol that are less than about 0.6," for example, it is meant that if the concentration by weight of glycerin is (about) 30%, then the concentration by weight of C2-C3 monoalcohol is more than (about) 50% by weight. In certain other embodiments of the invention, compositions of the present invention have ratios by weight of glycerin to C2-C4 monoalcohol that is from about 0.1 to about 0.25.

Cellulose Polymer

In accordance with the present invention, compositions for removing nail polish comprising at least one cellulose-based polymeric thickening agent are provided. Non-limiting examples of thickening agents that may be used according to various embodiments of the present invention include those conventionally used in cosmetics.

Suitable cellulose-based compounds include, but are not limited to, cellulose polymers, such as those modified with alkyl and/or hydroxyl functionality, for example, hydroxyethylcellulose, hydroxypropylcellulose, methylcellulose, and hydroxypropylmethylcellulose, ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g., KLUCEL MF—both available from Ashland of Covington, Ky. and METHOCEL—available from DuPont.

The at least one thickening cellulose-based polymer may be present in the compositions of the present invention in an amount greater than 0.05% by weight, such as greater than 0.1% by weight, such as greater than 0.5% by weight, such as greater than 1% by weight and may be less than 15% by weight, including all ranges and subranges therebetween such as, for example, from about 0.1% to about 15%, such as from about 0.1% to about 10%, such as from about 0.5% to about 10%, such as from about 0.75% to about 7.5%, such as from about 1% to about 5%, etc., with all weights being based on the weight of the composition.

While in certain notable embodiments, the composition is a single phase, in certain other embodiments, the composition may comprise multiple phases.

According to certain other embodiments, the composition may comprise a (e.g., a single) multicomponent solution phase including the co-mixture, and a suspended solid phase that is suspended in the multicomponent solution phase. The suspended solid phase may include any of various ingredients that do not dissolve in the multicomponent solution phase and are capable of being suspended therein. According to certain notable embodiments, the suspended solid phase includes one or more abrasive compounds.

Abrasive Compound

In accordance with the present invention, compositions for removing nail polish comprising at least one abrasive compound (abrasive system) are provided. A "abrasive compound" is a compound capable of providing abrasion or mechanical exfoliation and in accordance with the present invention has one or more of the following characteristics: (1) Surface roughness: particles with irregular edges provide for abrasion; (2) shape: the particles of the abrasive compound may have a non-angular shape such as a disc, oval or sphere; (3) average particle size: in the context of abrasive compounds from mineral origins, shells, seeds micronized fruit kernel powders, and the like. The particles of the abrasive may have a particle size of 1000 microns (μm) or less, such as 500 μm or less, such as 300 μm or less, such as 150 μm or less, such as 75 μm or less, such as, 50 μm or less such as 30 μm or less; and (4) hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrubeads), as well as synthetic polymeric materials such as polyethylene, polypropylene, polyethylene terephthalate, polymethyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

The suspended solid phase may include other particulate material such as pigments, optical modifiers, tactile modifiers, and the like.

Compositions of the present invention have a concentration by weight of water in the composition that is less than the concentration by weight of glycerin. According to certain other embodiments, compositions of the present invention may be essentially free of water, and in certain other embodiments, substantially free of water.

In certain embodiments of the invention are essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

The compositions according to the invention can be manufactured by known processes used generally in the cosmetics or dermatological field.

According to certain embodiments, methods of removing nail polish from nails comprising applying a composition for removing nail polish described above to nails onto which nail polish has been previously applied and removing the nail polish from the nails are provided.

According to certain other embodiments, methods of removing nail polish from nails (and optionally moisturizing hands) include the steps of applying a composition for removing nail polish described above to the hands as well as to the nails onto which nail polish has been previously applied; and removing the nail polish from the nails. The composition may also be rinsed from the hands and nails such as with water. In certain embodiments, compositions of the present invention may be advantageously used without an absorbent pad (otherwise commonly used to remove nail polish from the nails). As a result of the thickened consistency of the inventive compositions, they may also have reduced tendency to spill.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I(a)—Removability

An experiment was conducted to assess removability of nail polish using sixteen compositions including ethanol, acetone, and glycerin. Sixteen mixtures of ethanol, glycerin, and acetone were prepared by combining the ingredients in the relative concentrations by weight listed below and mixing on high speed vortex for 10 seconds.

Six mm draw down cards were prepared using ESSIE Russian Roulette nail lacquer available from L'Oreal SA of Paris, France. The cards were allowed to dry for 24 hours.

Mixtures were stirred with a spatula, and one spatula scoop of mixture was placed on a cotton pad. The pad was folded in half three times, and the card was wiped until the polish was removed, counting the number of strokes needed. The observation was recorded in Table 1, below:

TABLE 1

Nail Polish Removability for Acetone/Ethanol/Glycerin System

| Ref. | Acetone Conc. | Ethanol Conc. | Glyc. Conc. | Glyc./ Ethanol Ratio | Glyc./ Acetone Ratio | # of Wipes To Remove |
|---|---|---|---|---|---|---|
| A | 60 | 20 | 20 | 1.00 | 0.33 | — |
| B | 20 | 20 | 60 | 3.00 | 3.00 | 100+ |
| C | 30 | 45 | 25 | 0.56 | 0.83 | 10 |
| D | 45 | 45 | 10 | 0.22 | 0.22 | 4 |
| E | 30 | 25 | 45 | 1.80 | 1.50 | 31 |
| F | 34.8 | 32.7 | 32.6 | 1.00 | 0.94 | 8 |
| G | 34.6 | 28.0 | 37.4 | 1.33 | 1.08 | 11 |
| H | 30.9 | 28.1 | 41.0 | 1.46 | 1.33 | 10 |
| I | 37.7 | 20.2 | 42.1 | 2.09 | 1.12 | 18 |
| J | | | | | | |
| K | 25 | 36 | 39 | 1.08 | 1.56 | 27 |
| L | 33 | 28 | 39 | 1.39 | 1.18 | 25 |
| M | 20 | 45 | 35 | 1.57 | 0.285 | 26 |
| N | 20 | 45 | 35 | 0.78 | 1.75 | 25 |
| O | 25 | 55 | 20 | 0.36 | 0.80 | 36 |
| P | 15 | 70 | 15 | 0.21 | 1.00 | 8 |
| Q | 30 | 0 | 70 | — | 2.33 | 18 |

Example I(b)—Removability

An experiment was conducted to assess removability of nail polish, similarly to Example I(a), using seventeen compositions including ethanol, ethyl acetate, and glycerin. The observations were recorded in Table 2, below:

TABLE 2

Nail Polish Removability for Ethyl Acetate/Ethanol/Glycerin System

| Ref. | E Conc. | Ethanol Conc. | Glyc. Conc. | Glyc./ Ethanol Ratio | Glyc./ Acetone Ratio | # of Wipes To Remove |
|---|---|---|---|---|---|---|
| A | 30 | 40 | 30 | 0.75 | 1.00 | — |
| B | 30 | 45 | 25 | 0.55 | 0.83 | 20 |
| C | 30 | 45 | 25 | 1.80 | 1.5 | — |
| D | 40 | 15 | 45 | 3.00 | 1.12 | 100+ |
| E | 25 | 25 | 50 | 2.00 | 2.00 | 22 |
| F | 20 | 35 | 45 | 1.285 | 2.25 | 50 |
| G | 20 | 15 | 65 | 4.33 | 3.25 | 100+ |
| H | 20 | 45 | 35 | 0.78 | 1.33 | 55 |
| I | 20 | 25 | 55 | 2.20 | 2.75 | 27 |
| J | 15 | 30 | 55 | 1.83 | 3.67 | 55 |
| K | 25 | 35 | 40 | 1.14 | 1.60 | 39 |
| L | 30 | 10 | 60 | 6.00 | 2.00 | 100+ |
| M | 25 | 20 | 55 | 2.75 | 2.20 | 45 |
| N | 10 | 40 | 50 | 1.25 | 5.00 | 38 |
| O | 15 | 55 | 30 | 0.54 | 2.00 | 48 |
| P | 55 | 35 | 10 | 0.285 | 0.18 | — |
| Q | 20 | 60 | 20 | 0.33 | 1.00 | — |

Example II(a)—Phase Stability

The sixteen co-mixtures mixtures of ethanol, glycerin, and acetone above were prepared as above (in Example I(a) by combining the ingredients in the relative concentrations by weight listed below and mixing on high speed vortex for 10 seconds.

A first test formulation was prepared for adding sufficient SEPIGEL 305 to the co-mixture to yield 4% by weight SEPIGEL 305 (1.6% active polyacrylamide) and mixed in an attempt to produce a stable thickened composition. The mixtures were evaluated after one hour and twenty-four hours by visually assessing the thickened appearance/phase stability of the mixtures, looking for visible phase separation or solvent syneresis as an indication of instability. If a stable, thickened composition was produced a "Y" was recorded in the Table 3 below. Otherwise a "N" (no) was recorded.

If the composition was not thickened and phase stable, a second composition was prepared by adding sufficient SEPIGEL 305 to the co-mixture to yield 4% by weight SEPIGEL 305 and adding sufficient water to the co-mixture to yield 4% by weight of water. If a stable, thickened composition was produced a "Y" was recorded in the Table 3 below. Otherwise a "N" (no) was recorded.

If this second composition was not thickened and phase stable, a third composition was prepared by adding sufficient KLUCEL MF PHARM (100% active hydroxypropylcellulose) to the co-mixture to yield 4% by weight of hydroxypropylcellulose. If a stable, thickened composition was produced a "Y" was recorded in the Table 3 below. Otherwise a "N" (no) was recorded.

A first test formulation was prepared for adding sufficient SEPIGEL 305 to the co-mixture to yield 4% by weight SEPIGEL 305 (1.6% active polyacrylamide) and mixed in an attempt to produce a stable thickened composition.

The results are indicated in Table 3, below. If a stable, thickened composition was produced a "Y" was recorded in the Table 3 below. Otherwise a "N" (no) was recorded.

If the composition was not thickened and phase stable, a second composition was prepared by adding sufficient SEPIGEL 305 to the co-mixture to yield 4% by weight SEPIGEL 305 and adding sufficient water to the co-mixture to yield 4% by weight of water. If a stable, thickened composition was produced a "Y" was recorded in the Table 3 below. Otherwise a "N" (no) was recorded. Table 3 also shows concentrations by weight of ethanol, glycerin, and acetone in the co-mixture, as well as glycerin to acetone weight ratio and glycerin to ethanol weight ratio.

TABLE 3

Thickening/Stability for Acetone/Ethanol/Glycerin System

| Ref. | Acetone Conc. | Ethanol Conc. | Glyc. Conc. | Glyc./ Ethanol Ratio | Glyc./ Acetone Ratio | Stable/ Thickened PA, No water (Y/N) | Stable/ Thickened PA, Plus water (Y/N) | Stable/ Thickened Cellulose (Y/N) |
|---|---|---|---|---|---|---|---|---|
| A | 60 | 20 | 20 | 1.00 | 0.33 | N | N | N |
| B | 20 | 20 | 60 | 3.00 | 3.00 | Y | | |
| C | 30 | 45 | 25 | 0.56 | 0.83 | N | Y | |

TABLE 3-continued

Thickening/Stability for Acetone/Ethanol/Glycerin System

| Ref. | Acetone Conc. | Ethanol Conc. | Glyc. Conc. | Glyc./ Ethanol Ratio | Glyc./ Acetone Ratio | Stable/ Thickened PA, No water (Y/N) | Stable/ Thickened PA, Plus water (Y/N) | Stable/ Thickened Cellulose (Y/N) |
|---|---|---|---|---|---|---|---|---|
| D | 45   | 45   | 10   | 0.22 | 0.22  | N | Y |   |
| E | 30   | 25   | 45   | 1.80 | 1.50  | Y |   |   |
| F | 34.8 | 32.7 | 32.6 | 1.00 | 0.94  | N | Y |   |
| G | 34.6 | 28.0 | 37.4 | 1.33 | 1.08  | N | Y |   |
| H | 30.9 | 28.1 | 41.0 | 1.46 | 1.33  | Y |   |   |
| I | 37.7 | 20.2 | 42.1 | 2.09 | 1.12  | N | Y |   |
| K | 25   | 36   | 39   | 1.08 | 1.56  | Y |   |   |
| L | 33   | 28   | 39   | 1.39 | 1.18  | N | Y |   |
| M | 20   | 45   | 35   | 1.57 | 0.285 | Y |   |   |
| N | 20   | 45   | 35   | 0.78 | 1.75  | Y |   |   |
| O | 25   | 55   | 20   | 0.36 | 0.80  | N | N | Y |
| P | 15   | 70   | 15   | 0.21 | 1.00  | N | N | Y |
| Q | 30   | 0    | 70   | —    | 2.33  | N | Y |   |

The sixteen mixtures of ethanol, glycerin, and ethyl acetate above were prepared as above (in Example I(b)) by combining the ingredients in the relative concentrations by weight listed below and mixing on high speed vortex for 10 seconds. The mixtures were evaluated after one hour and twenty-four hours by visually assessing the thickened appearance/phase stability of the mixtures, looking for visible phase separation or solvent syneresis as an indication of instability. If a stable, thickened composition was produced a "Y" was recorded in the Table 3 below. Otherwise a "N" (no) was recorded.

If the composition was not thickened and phase stable, a second composition was prepared by adding sufficient SEPIGEL 305 to the co-mixture to yield 4% by weight SEPIGEL 305 and adding sufficient water to the co-mixture to yield 4% by weight of water. If a stable, thickened composition was produced a "Y" was recorded in the Table 4 below. Otherwise a "N" (no) was recorded. Table 4 also shows concentrations by weight of ethanol, glycerin, and ethyl acetate (EtAc) in the co-mixture, as well as glycerin to ethyl acetate weight ratio and glycerin to ethanol weight ratio.

The results are further displayed in FIG. 1 (acetone) and FIG. 2 (ethyl acetate), which are essentially diagrams depicting the results of thickening/stability testing for particular compositions. Circles indicate compositions which were successfully thickened with polyacrylamide (no added water). Squares indicate compositions that were successfully thickened with polyacrylamide with 4% added water but were not successfully thickened with polyacrylamide with no added. Furthermore, for FIG. 1, triangles indicate compositions which were successfully thickened with cellulose polymer but were not successfully thickened with polyacrylamide (either with no added or with added water). Diamonds indicate compositions that were not successfully thickened with polyacrylamide, nor with polyacrylamide with added water, nor with cellulose polymer.

What is claimed is:
1. A composition for removing nail polish comprising:
a solution phase comprising a co-mixture consisting of:
  from about 30% to about 70% by weight of the co-mixture of C2-C3 monoalcohol;
  from about 5% to about 25% by weight of the co-mixture of glycerin; and

TABLE 4

Thickening/Stability for Ethyl Acetate (EtAc)/Ethanol/Glycerin System

| Ref. | EtAc Conc. | Ethanol Conc. | Glyc. Conc. | Glyc./ Ethanol Ratio | Glyc./ EtAc Ratio | Stable/ Thickened PA, No water (Y/N) | Stable/ Thickened PA, Plus water (Y/N) |
|---|---|---|---|---|---|---|---|
| A | 30 | 40 | 30 | 0.75  | 1.00 | N | N |
| B | 30 | 45 | 25 | 0.55  | 0.83 | N | Y |
| C | 30 | 45 | 25 | 1.80  | 1.5  | N | N |
| D | 40 | 15 | 45 | 3.00  | 1.12 | N | Y |
| E | 25 | 25 | 50 | 2.00  | 2.00 | Y |   |
| F | 20 | 35 | 45 | 1.285 | 2.25 | Y |   |
| G | 20 | 15 | 65 | 4.33  | 3.25 | Y |   |
| H | 20 | 45 | 35 | 0.78  | 1.33 | N | Y |
| I | 20 | 25 | 55 | 2.20  | 2.75 | Y |   |
| J | 15 | 30 | 55 | 1.83  | 3.67 | Y |   |
| K | 25 | 35 | 40 | 1.14  | 1.60 | N | N |
| L | 30 | 10 | 60 | 6.00  | 2.00 | N | N |
| M | 25 | 20 | 55 | 2.75  | 2.20 | Y |   |
| N | 10 | 40 | 50 | 1.25  | 5.00 | Y |   |
| O | 15 | 55 | 30 | 0.54  | 2.00 | N | Y |
| P | 55 | 35 | 10 | 0.285 | 0.18 | N | N |
| Q | 20 | 60 | 20 | 0.33  | 1.00 | N | N | from about 10% to about 45% by weight of the co-mixture of acetone;

wherein the glycerin and the C2-C3 monoalcohol are present in a glycerin to C2-C3 monoalcohol weight ratio of less than about 0.6;
a cellulose polymer soluble in said C2-C3 monoalcohol;
a suspended solid phase comprising at least one abrasive compound in the solution phase; and
optionally water and/or oil;

wherein a concentration by weight of water in the composition, if present, is less than a concentration by weight of glycerin in the composition, and, wherein water and/or oil, if present, are each independently present in the composition in an amount of less than about 3% by weight of the composition.

2. The composition of claim 1, wherein the co-mixture comprises from about 10% to about 40% by weight of the co-mixture of acetone.

3. The composition of claim 1, wherein the glycerin to C2-C3 monoalcohol weight ratio is between about 0.1 and about 0.25.

4. The composition of claim 1, wherein the cellulose polymer is modified with alkyl and/or hydroxyl functionality.

5. The composition of claim 1, wherein the cellulose polymer is a hydroxypropylcellulose.

6. The composition of claim 1, wherein the glycerin and the acetone are present in a glycerin to acetone weight ratio of less than 1.2.

7. The composition of claim 1, wherein the C2-C3 monoalcohol is ethanol.

8. The composition of claim 1, wherein the glycerin is present in the co-mixture in a concentration by weight of from about 15% to about 25% of the co-mixture.

9. The composition of claim 1, wherein the C2-C3 monoalcohol is present in the co-mixture in a concentration by weight from about 45% to about 70% of the co-mixture.

10. The composition of claim 1, wherein the cellulose polymer is present in a concentration from about 0.75% to 7.5% by weight of the composition.

11. The composition of claim 1, wherein the C2-C3 monoalcohol is ethanol, and wherein the concentration of ethanol in the co-mixture is from about 45% to about 70% by weight of the co-mixture.

12. The composition of claim 1, wherein the C2-C3 monoalcohol is ethanol, wherein the concentration of ethanol in the co-mixture is from about 45% to about 70% by weight of the co-mixture, and wherein the cellulose polymer is a hydroxypropylcellulose.

13. The composition of claim 1, wherein the C2-C3 monoalcohol is ethanol, wherein the concentration of ethanol in the co-mixture is from about 45% to about 70% by weight of the co-mixture, wherein the co-mixture comprises from about 10% to about 40% by weight of the co-mixture of acetone; and wherein the cellulose polymer is a hydroxypropylcellulose.

14. A method of removing nail polish from nails and moisturizing the hands of a subject, comprising:
applying the composition of claim 1 to hands and to nails of a subject onto which the nail polish had been previously applied, and
removing the nail polish from the nails.

15. The method of claim 14, wherein the co-mixture comprises from about 10% to about 40% by weight of the co-mixture of acetone.

16. The method of claim 14, wherein the cellulose polymer is modified with alkyl and/or hydroxyl functionality.

17. The method of claim 14, wherein the C2-C3 monoalcohol is ethanol, wherein the concentration of ethanol in the co-mixture is from about 45% to about 70% by weight of the co-mixture, and wherein the cellulose polymer is a hydroxypropylcellulose.

18. A composition for removing nail polish comprising:
a solution phase comprising a co-mixture consisting of:
from about 30% to about 70% by weight of the co-mixture of C2-C3 monoalcohol;
from about 5% to about 25% by weight of the co-mixture of glycerin; and
from about 10% to about 45% by weight of the co-mixture of acetone;
wherein the glycerin and the C2-C3 monoalcohol are present in a glycerin to C2-C3 monoalcohol weight ratio of less than about 0.6;
a cellulose polymer soluble in said C2-C3 monoalcohol;
a suspended solid phase comprising at least one abrasive compound in the solution phase; and
optionally water;
wherein a concentration by weight of water in the composition, if present, is less than a concentration by weight of glycerin in the composition, and
wherein the composition does not have visible phase separation or solvent syneresis.

19. The composition of claim 1, wherein water and/or oil, if present, are each independently present in the composition in an amount of less than about 2% by weight of the composition.

* * * * *